United States Patent
Wilson et al.

(10) Patent No.: US 7,060,086 B2
(45) Date of Patent: Jun. 13, 2006

(54) THERMAL TREATMENT PACK

(75) Inventors: Jeffrey Alan Wilson, Cleveland Heights, OH (US); Jonathan Wendell Flick, Mentor, OH (US)

(73) Assignee: Wendell-Alan, Ltd., Cleveland, OH (US)

( * ) Notice: Subject to any disclaimer, the term of this patent is extended or adjusted under 35 U.S.C. 154(b) by 370 days.

(21) Appl. No.: 10/298,453

(22) Filed: Nov. 18, 2002

(65) Prior Publication Data

US 2004/0098073 A1 May 20, 2004

(51) Int. Cl.
*A61F 7/00* (2006.01)

(52) U.S. Cl. .......................... 607/108; 607/114; 602/63
(58) Field of Classification Search ......... 607/108–112, 607/114, 96; 602/60–65
See application file for complete search history.

(56) References Cited

U.S. PATENT DOCUMENTS

| | | | |
|---|---|---|---|
| 3,934,583 A | | 1/1976 | Hollingshead et al. |
| 4,910,978 A | * | 3/1990 | Gordon et al. ................ 62/530 |
| RE34,661 E | | 7/1994 | Grim |
| 5,356,426 A | | 10/1994 | Delk et al. |
| 5,389,065 A | | 2/1995 | Johnson, Jr. |
| 5,411,541 A | | 5/1995 | Bell et al. |
| RE35,113 E | | 12/1995 | Grim |
| 5,486,206 A | * | 1/1996 | Avery ......................... 607/104 |
| 5,843,145 A | * | 12/1998 | Brink .......................... 607/114 |
| 6,401,247 B1 | * | 6/2002 | Williams, IV .................... 2/59 |
| D464,140 S | | 10/2002 | Lavin, Jr. |
| 6,623,426 B1 | * | 9/2003 | Bonadio et al. ............ 600/207 |
| 2002/0103520 A1 | | 8/2002 | Latham |

FOREIGN PATENT DOCUMENTS

EP    1038510 A2    9/2000

OTHER PUBLICATIONS

Pufferbelly Toys web page (undated) depicting and describing "water snake" novelty toy available from Toysmith, Inc.

* cited by examiner

*Primary Examiner*—John P. Leubecker
(74) *Attorney, Agent, or Firm*—Rankin, Hill, Porter & Clark LLP (57) ABSTRACT

The present invention provides a thermal treatment pack that includes a tubular body having a first opening, a second opening, an inner surface and an outer surface. The first opening, the inner surface and the second opening cooperate to define a passage through the tubular body for the limb. The inner surface and the outer surface of the tubular body are defined by a continuous film of flexible material such as a copolymer of polyester and polyurethane. A temperature-retaining fluid such as a water-based gel is received between the inner surface and the outer surface. Optionally, a thermal pack according to the invention can be covered with a fabric layer to provide insulation between the continuous film of flexible material and a user's skin. The diameter of the passage through the thermal treatment pack is preferably smaller than or equal to the diameter of the injured limb, which causes the inner surface of the thermal treatment pack to make contact the limb or an insulating wrap placed over the limb. The thermal treatment pack can thus be positioned at the desired location on the limb by rolling the thermal treatment pack onto the limb. During rolling, the continuous film of flexible material frictionally engages the limb and does not move relative to the limb as the thermal treatment pack is rolled onto the limb. The continuous film of flexible material stretches and conforms to the shape of the limb, providing compressive force and circumferential thermal treatment at the desired location.

31 Claims, 7 Drawing Sheets

THERMAL TREATMENT PACK

BACKGROUND OF THE INVENTION

1. Field of Invention

The present invention relates to a thermal treatment pack, and more particularly, to a thermal treatment pack that can be positioned on a user's limb to provide circumferential thermal treatment and compression at a desired location on the limb.

2. Description of Related Art

The generally accepted first aid treatment for strains, sprains, contusions, dislocations, uncomplicated fractures and other non-acute injuries to human limbs is often referred to by the acronym RICE, which stands for rest, ice, compression and elevation. Rest is prescribed because continued activity can cause further injury to the limb thereby delaying the healing process, increasing pain, and stimulating internal bleeding. Ice is prescribed because blood vessels contract when exposed to cold temperatures, which helps reduce swelling in the injured limb and also helps to reduce the extent of internal bleeding from injured capillaries and blood vessels. Compression is prescribed because it tends to hasten healing time by reducing swelling around injury. And, elevation of the limb above the heart is prescribed because it tends to reduce swelling in the limb and also tends to reduce pain.

Although ice is prescribed to treat injured limbs, ice can cause discomfort when placed between a compressive wrap and an injured limb because it is a rigid non-conforming solid. Ice is also difficult to position on an injured limb and it tends to melt quickly, which results in a loss of the desired cold treatment and/or frequent disturbance of the injured limb to apply more ice. In view of these and other disadvantages, temperature-retaining gel-filled thermal packs are frequently used instead of ice in the first aid treatment of injured limbs. The gels used in such packs tend to remain cold for a longer period of time than ice, and such gels also preferably remain viscous at low temperatures, which allow them to more comfortably conform to the contours of the injured limb when placed between a compressive wrap and the injured limb.

Conventional gel-filled thermal treatment packs generally consist of a substantially flat flexible envelope that has been filled with a temperature-retaining gel material. Pre-chilled "flat packs" of this type are typically pressed into contact with an injured limb and over-wrapped with a suitable material such as an elastic bandage to hold it in place and provide compression to the injured limb. Some gel-filled thermal treatment packs are provided with straps or other means of securing the flat pack in contact with the injured limb.

Flat packs, while widely used to provide first aid treatment to injured limbs, present certain problems and disadvantages. One problem with flat packs is that they do not provide circumferential thermal treatment to injured limbs (i.e., thermal treatment completely surrounding the injured limb at the location of the injury). Flat packs are effective in applying cold treatment to injured limbs only insofar as they can be placed into contact with the injured limb. Thus, in order to provide circumferential or radial thermal treatment to an injured limb, it is typically necessary to apply more than one flat pack to the injured limb, which can present placement and retention problems. In addition, it is sometimes very difficult and time consuming to secure flat packs to an injured limb, even when the flat pack is provided with straps or other securing means.

BRIEF SUMMARY OF THE INVENTION

The present invention provides a thermal treatment pack that can be positioned onto a user's limb to provide circumferential thermal treatment. A thermal treatment pack in accordance with the invention comprises a tubular body having a first opening, a second opening, an inner surface and an outer surface. The first opening, the inner surface and the second opening cooperate to define a passage through the tubular body for the limb. The inner surface and the outer surface of the tubular body are defined by a continuous film of flexible material such as, for example, a copolymer of polyester and polyurethane. A temperature-retaining fluid such as a water-based gel is received between the inner surface and the outer surface. In one preferred embodiment, a selectively pressurizable radial air bladder is formed on the outer surface of the tubular body to provide circumferential compression and support for the limb. Optionally, a thermal pack according to the invention can be covered with a fabric layer to provide an insulation layer between the continuous film of flexible material and the user's skin.

The present invention also provides a method of treating an injured limb. The method according to the invention comprises providing a thermal treatment pack in accordance with the invention, inserting the injured limb into the passage through the tubular body of the thermal treatment pack, and positioning the thermal treatment pack on the limb at a location where compression and circumferential thermal treatment is desired. The diameter of the passage through the thermal treatment pack is preferably smaller than or equal to the diameter of the injured limb, which causes the inner surface of the thermal treatment pack to make contact the limb or an insulating wrap placed over the limb. Alternatively, the diameter of the passage through the thermal treatment pack is larger than the diameter of the limb, and the thermal treatment pack further comprises a radial air bladder that can be inflated to press the inner surface of the thermal treatment pack into contact with the limb or the insulating wrap placed over the limb.

The thermal treatment pack according to the invention can be positioned at the desired location on the limb simply by rolling the thermal treatment pack onto the limb. During rolling, the continuous film of flexible material frictionally engages the limb and does not move relative to the limb as the thermal treatment pack is rolled onto the limb. The continuous film of flexible material stretches and conforms to the shape of the limb, providing compressive force and circumferential thermal treatment at the desired location. The thermal treatment pack according to the invention can be retained in the desired location on the injured limb without the need for additional securing means or over-wrapping, and thus can be quickly and easily installed by a user using one hand. This allows for easy self-treatment of injured limbs.

The present invention also provides a method of manufacturing a thermal treatment pack. The method of manufacturing a thermal treatment pack according to the invention comprises: forming a film of flexible material into a tube having a first edge defining a first open end and an opposing second edge defining a second open end; folding the tube such that the first edge and the second edge are concentric to each other; and sealing the first edge to the second edge to form a tubular body having a first opening, a second opening, an inner surface and an outer surface, wherein the first opening, the inner surface and the second opening cooperate to define a passage through the tubular body for a limb. A temperature-retaining fluid is disposed into a space between the inner surface and the outer surface before or after the first edge and the second edge are sealed to form the tubular body.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

Figure 1:
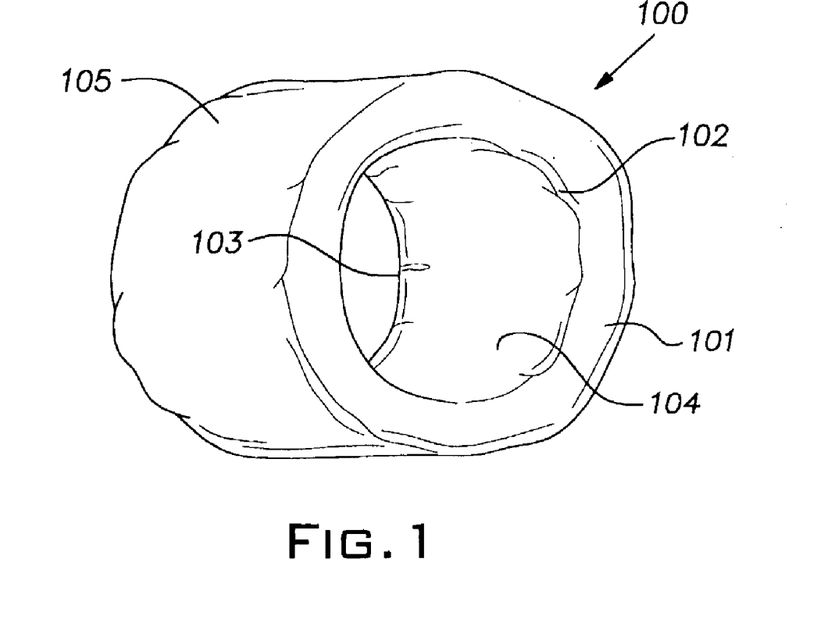
FIG. 1 is a perspective view of one exemplary embodiment of a thermal treatment pack according to the invention.
Figure 2:
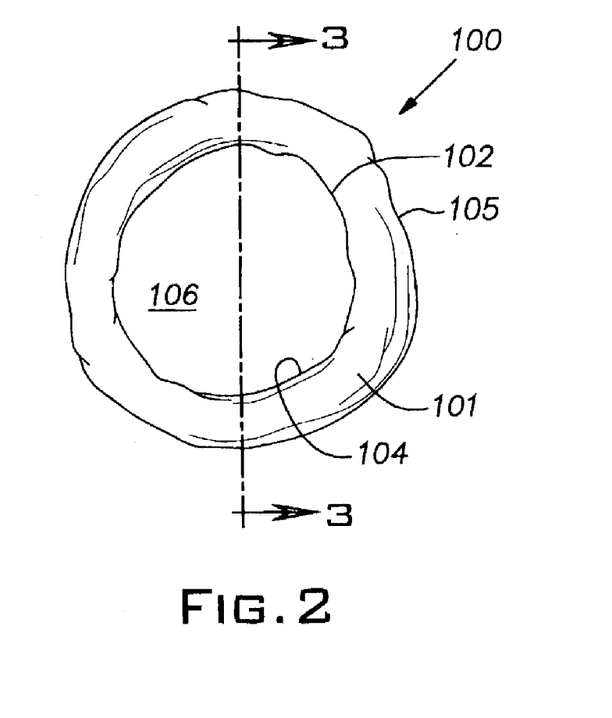
FIG. 2 is a view of the thermal treatment pack as seen along the line II in FIG. 1.
Figure 3:
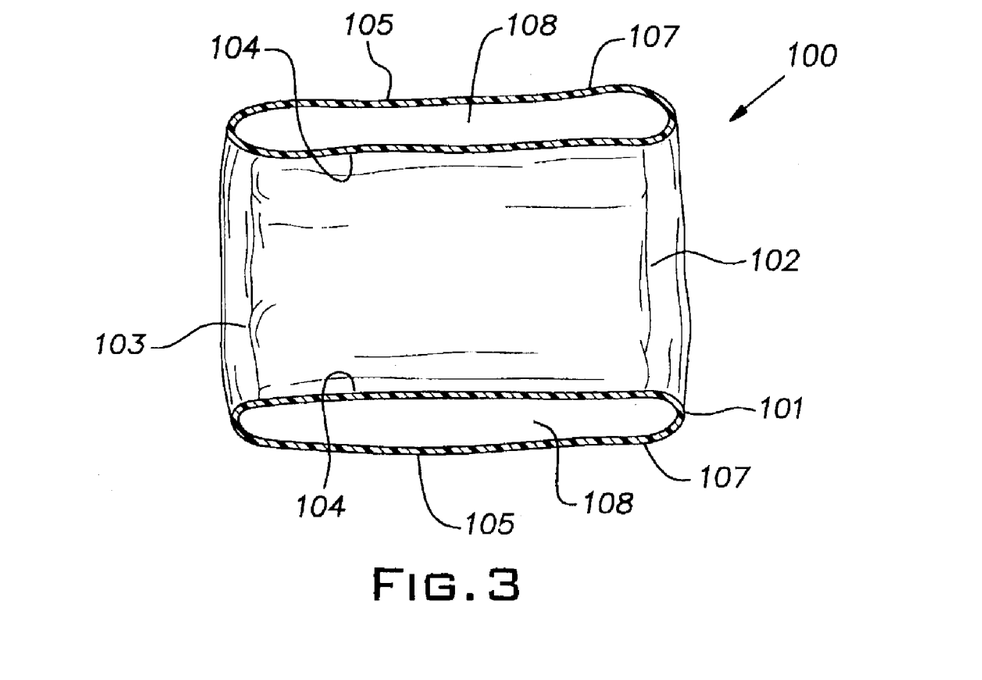
FIG. 3 is a cross-sectional view of the thermal treatment pack taken along the line III—III in FIG. 2.

With reference to FIGS. 1 and 2, a thermal treatment pack 100 according to the invention comprises a tubular body 101 having a first opening 102, a second opening 103, an inner surface 104 and an outer surface 105. The first opening 102, the inner surface 104 and the second opening 103 cooperate to define a passage 106 through the tubular body 101 for a limb. FIG. 3 is a view of the thermal treatment pack 100 as seen along the line III in FIG. 2. Thus, a thermal treatment pack in accordance with the invention has an elongated generally torus-like shape.

The inner surface 104 and the outer surface 105 are formed of and defined by a continuous film of flexible material 107. The continuous film of flexible material 107 is preferably a polymeric film that remains flexible over a relatively broad temperature range of from about 0° F. to about 130° F. A large number of polymeric films that remain flexible over such a temperature range are known in the art. It will be appreciated that polymeric films used in the invention can be single layer films or multi-layer structures.

Preferably, the continuous film of flexible material exhibits a Shore A durometer hardness of greater than or equal to 85 as measured in accordance with the ASTM 2240.00 standard. More preferably, the continuous film of flexible material exhibits a Shore A durometer hardness of 93±5 as measured in accordance with the ASTM 2240.00 standard. Films possessing such properties are advantageously puncture resistant yet remain flexible.

The continuous film of flexible material preferably has a thickness of from about 3 to about 15 mils. More preferably, the continuous film of flexible material has a thickness of 5±2 mils. It will be appreciated that film thickness is not per se critical, and that a variety of film thicknesses can be used to fabricate a thermal treatment pack in accordance with the invention.

In the presently most preferred embodiment of the invention, the continuous film of flexible material comprises a 5 mil thick copolymer of polyester and polyurethane having a Shore A durometer hardness of about 95 as measured in accordance with the ASTM 2240.00 standard. This film provides several advantages. It can be heat sealed to itself, which facilitates fabrication of the thermal treatment pack. It does not irritate human skin on contact. And, it remains smooth and flexible over the temperature range of from about 0° F. to about 130° F.

A temperature-retaining fluid 108 is received between the inner surface 104 and the outer surface 105. Throughout the instant specification and in the appended claims, the term "temperature-retaining fluid" means any material that changes shape or direction uniformly in response to an external force imposed upon it and that has the capacity to retain heat or cold for transfer to a limb. The term applies not only to liquids, but also to finely divided solids having such properties. Preferably, the temperature-retaining fluid is a gel, and more preferably a water-based gel.

Water-based gels can be formulated so as to provide a temperature-retaining fluid that is more viscous than water and does not become a hard solid within the temperature range of from 0° F. and 32° F. Such gels can conform to the contours of the injured limb more comfortably than ice. In addition, such gels tend to retain their desired thermal properties for a longer period of time than water. The gel-filled thermal treatment pack can be pre-heated or pre-chilled, depending upon the type of thermal treatment to be provided. The composition of the gel is not per se critical, but preferably a non-toxic formulation is used to minimize potential injury in the event of exposure.

In another embodiment of the invention, water-filled capsules are dispersed in the temperature-retaining fluid to extend the period of time during which the thermal pack remains cold. The water filled capsules are preferably small, such as the size of peas, and substantially spherical, which allows the thermal treatment pack to comfortably conform to limbs. Other free-flowing solid structures can be dispersed in the temperature-retaining fluid. Examples include particulates (e.g., sand and/or ceramic particles), spherical structures (e.g., glass and/or metal spheres), and magnets. It will be appreciated that virtually any relatively small substantially free-flowing solid structure can be dispersed in the temperature-retaining fluid, but water-filled capsules are preferably most preferred in view of cost, safety, and effectiveness.

It is often desirable to dispose a fabric layer between the limb and the thermal treatment pack, particularly when the thermal treatment pack has been pre-chilled. The fabric layer acts as an insulation layer, which prevents frostbite and/or burns. The fabric layer can be wrapped around the limb prior to applying the thermal treatment pack, or a fabric layer can be disposed on the thermal treatment pack so as to be coextensive with the inner surface and outer surface of the tubular body. In some applications, such as the treatment of an ankle injury, a sock can serve as the fabric layer.

Figure 4:
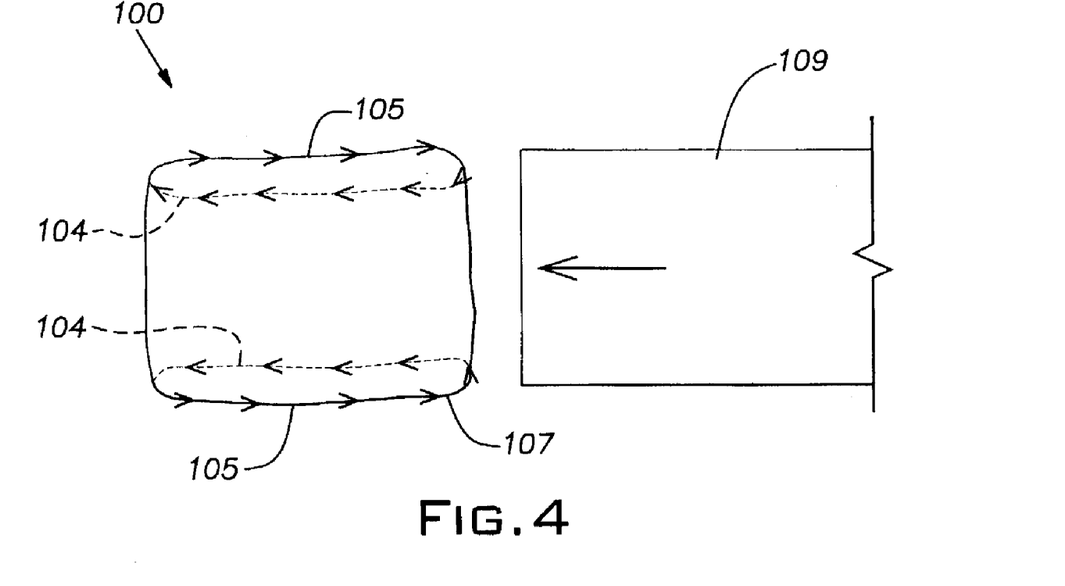
FIG. 4 is a schematic view of a thermal treatment pack according to the invention about to be rolled onto a limb.

FIG. 4 is a schematic view showing a thermal treatment pack 100 according to the invention as it is about to be placed onto a limb 109. The large arrow shown on the limb 109 shows the direction the limb moves relative to the thermal treatment pack 100. The series of small arrows shown on the inner surface 104 and the outer surface 105 of the thermal treatment pack 100 in FIG. 4 show the movement of the continuous film of flexible material 107 as the thermal treatment pack 100 is being placed on the limb 109. Preferably, the diameter of the passage 106 through the tubular body 101 is equal to or smaller than the diameter of the limb 109, which causes the continuous film of flexible material 107 to frictionally engage the limb 109, or a fabric layer disposed between the limb 109 and the continuous film of flexible material 107. Thus, the continuous film of flexible material 107 does not move substantially relative to the limb 109, but rather it everts as the thermal treatment pack 100 rolls up the limb 109 in the direction opposite the large arrow and retains its general shape. As shown by the series of arrows in FIG. 4, the continuous film of flexible material is eversion-limitless, meaning that the continuous film can evert around the tubular body from the inner surface to the outer surface and back an infinite number of cycles or revolutions.

Figures 5A, 5B:
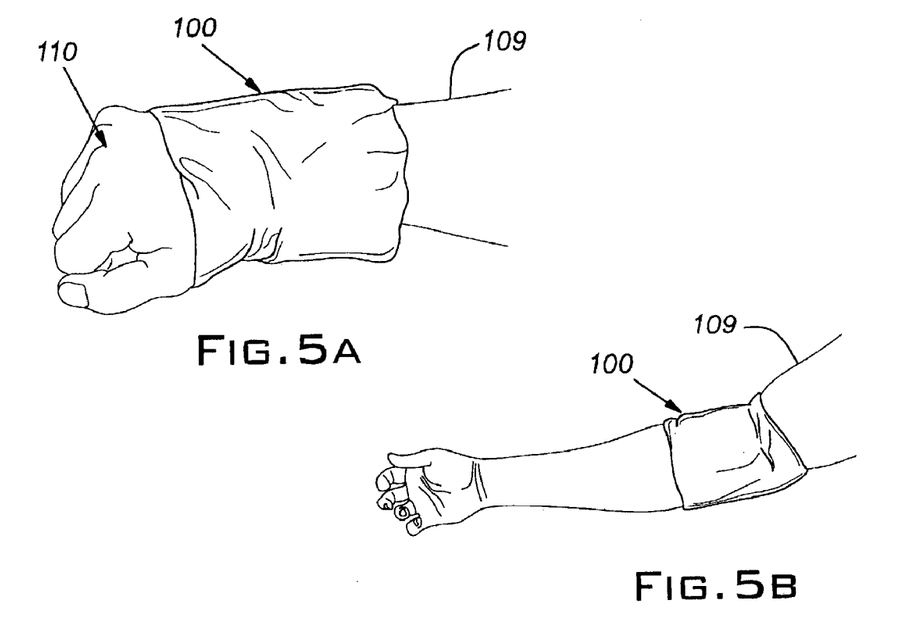
FIG. 5A is a perspective view of a thermal treatment pack according to the invention positioned on a wrist.
FIG. 5B is a perspective view of a thermal treatment pack according to the invention positioned on an elbow.

FIG. 5A shows a perspective view of a thermal treatment pack 100 positioned on a limb 109, which in this illustration is an arm. In this case, the user first inserted his hand 110 into the passage 106 through the tubular body 101 of the thermal treatment pack 100. The continuous film of flexible material 107 frictionally engaged the user's hand 110, causing the thermal treatment pack 100 to roll up the user's hand 110 to the desired location on the limb 109, which in this illustration is the user's wrist. The thermal treatment pack 100 thus provides circumferential thermal treatment and comfortable compression to the user's wrist.

It will be appreciated that the thermal treatment pack according to the invention can be formed with passages having various configurations depending upon the intended use. Thermal treatment packs according to the invention can be used to treat hands, wrists, elbows, forearms, upper arms, feet, ankles, calves, knees, and thighs. In order to insure proper compressive force is applied to the limb, it is important that the thermal treatment pack be properly sized. Larger sized thermal treatment packs can be used on legs, and smaller sized thermal treatment packs can be used on arms and children.

When configured for use on a wrist, the passage through the tubular body is preferably substantially cylindrical in shape with an inner diameter within the range of from about 2.5 to about 4.0 inches. The passage through the tubular body preferably has a length of from about 4.0 to about 6.0 inches. Approximately 16 ounces of gel material is disposed into the space between the inner surface and the outer surface, which results in a gel layer that is about 0.5 inches thick around the entire wrist when the thermal treatment pack is positioned on the user.

Figures 5C, 5D:
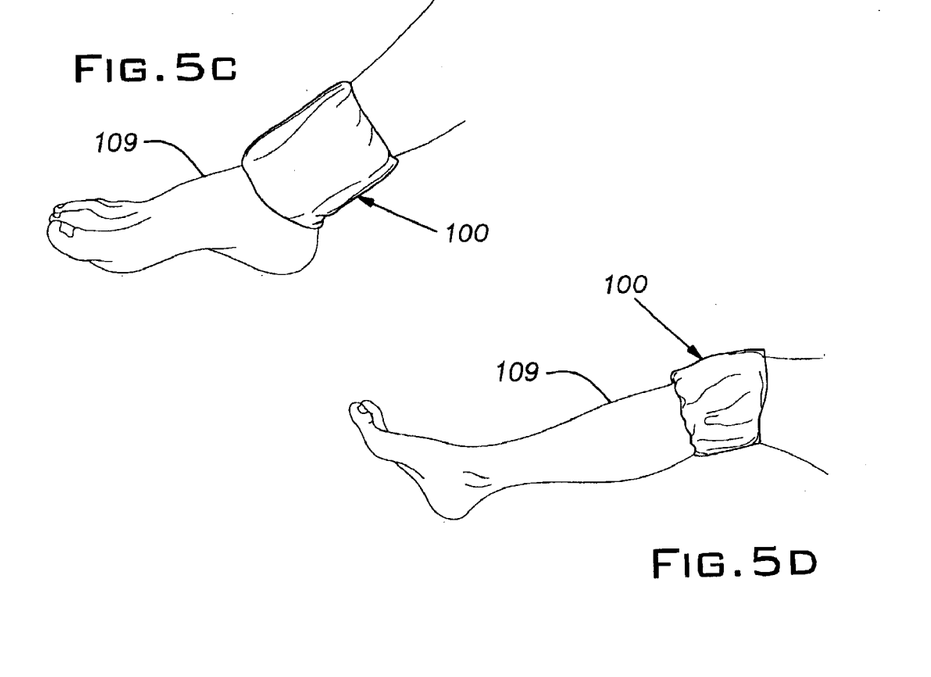
FIG. 5C is a perspective view of a thermal treatment pack according to the invention positioned on an ankle.
FIG. 5D is a perspective view of a thermal treatment pack according to the invention positioned on a knee.

Thermal treatment packs configured for use on an elbow generally have a passage through the tubular body that is larger in diameter and greater in length than a thermal treatment pack configured for use on a wrist. Thermal treatment packs configured for use on forearms preferably have a tapered passage. Thermal treatment packs configured for elbows (see FIG. 5B), ankles (see FIG. 5C), knees (see Fig. D), calves, thighs, and other body parts are preferably shaped and sized so as to be comfortable when positioned thereon. It will be appreciated that the size of the passage and the amount of gel disposed into the space between the inner surface and the outer surface can be adjusted to suit a particular end use application.

One of the advantages provided by the thermal treatment pack according to the invention is the ease by which it can be positioned on an injured limb. Because it is a self-securing device, the thermal treatment pack can be quickly positioned onto an injured limb using only one hand. No fasteners or over-wrap materials are necessary. And once the thermal treatment pack is rolled into the desired position, it remains in the desired position without the need for attachment devices. Thus, for example, a tennis player who injures his or her wrist can roll a pre-chilled thermal treatment pack into place over his or her wrist and then continue to play tennis. Similarly, a person suffering from cold or sore feet can roll a pre-heated thermal treatment pack onto his or her foot and enjoy the circumferential thermal and compressive benefits provided by it without having to hold the thermal treatment pack in place.

Figure 6:
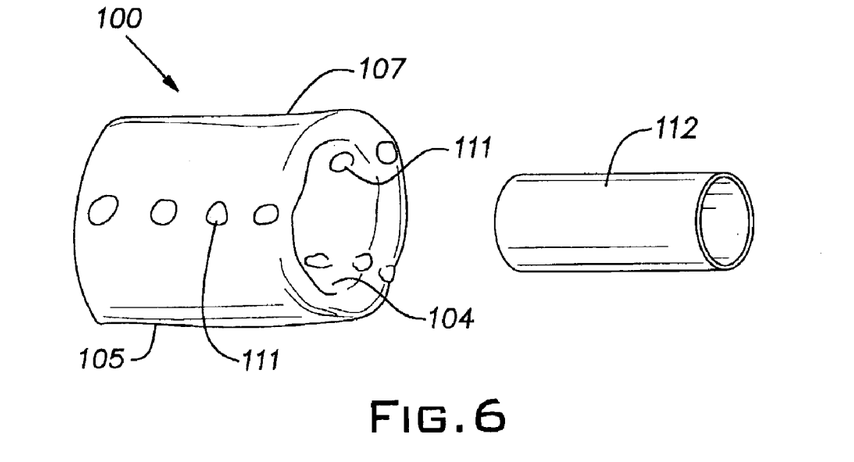
FIG. 6 is a perspective view of another exemplary embodiment of a thermal treatment pack and fabric sleeve according to the invention.

Although it is not necessary in most instances, it is possible to enhance the degree to which a thermal treatment pack remains positioned on a limb by use of hook and loop fastener material such as VELCRO. With reference to FIG. 6, hook material 111 can be affixed to the continuous film of flexible material 107 such that the hook material 111 is disposed on both the inner surface 104 and outer surface 105. An elastic tube or wrapping of loop material 112, such as terry cloth, can then placed around the limb where the thermal treatment pack 100 is to be positioned. Thus, when the thermal treatment pack 100 is positioned in the desired location on the limb, the hook material 111 disposed on the inner surface 104 engages the loop material 112, retaining the thermal treatment pack 100 in the desired position on the limb. The amount and configuration of the hook material 111 disposed on the inner surface 104 is not per se critical. In FIG. 6, the hook material 111 is shown as dots.

Figure 7A:
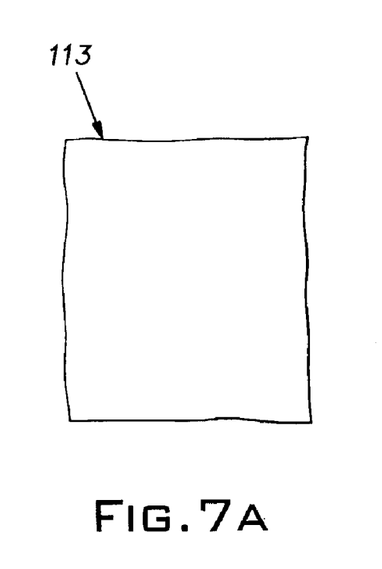
FIG. 7A is a schematic view of a film of flexible material for use in manufacturing a thermal treatment pack according to the invention.
Figure 7B:
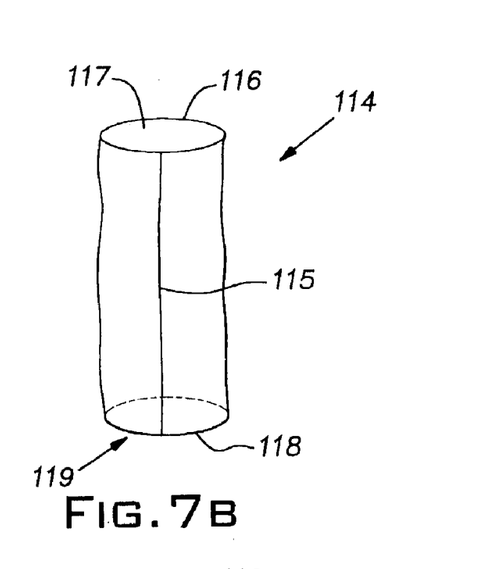
FIG. 7B is a schematic view showing the film in FIG. 7A formed into a tube.

The presently most preferred method of manufacturing a thermal treatment pack is illustrated in FIGS. 7A–7D. With reference to FIG. 7A, a sheet 113 of flexible material such as polyurethane film is cut into a desired shape and size. As shown in FIG. 7B, the sheet 113 is formed into a tube 114 by heat-sealing opposing edges of the sheet together to form a seam 115. Heat sealing can be accomplished using a hot wire sealer or other conventional heat sealing equipment.

Figure 8A:
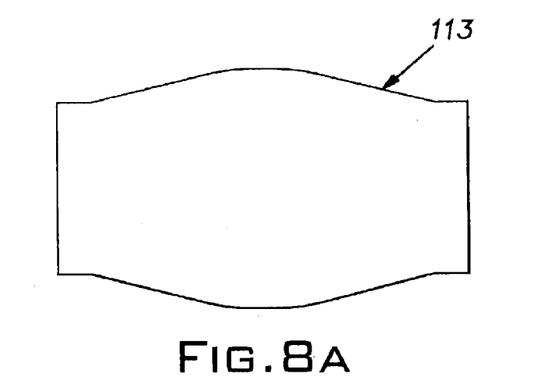
FIG. 8A is a schematic view of a reverse hour glass-shaped sheet of flexible material.
Figure 8B:
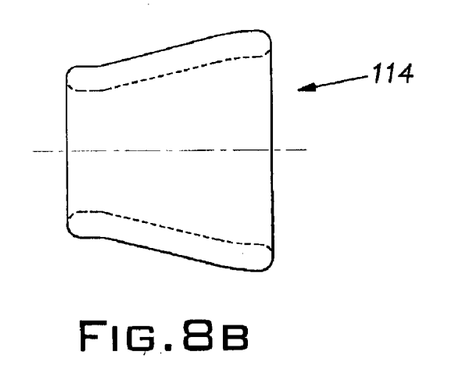
FIG. 8B is a schematic cross-sectional view of a tube formed from the sheet shown in FIG. 8A.
Figure 8C:
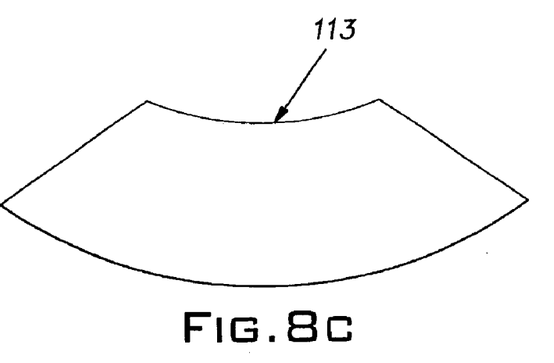
FIG. 8C is a schematic view of an arcuate-shaped sheet of flexible material.
Figure 8D:
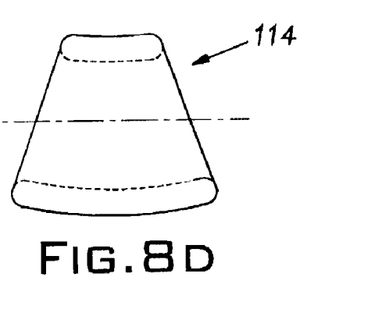
FIG. 8D is a schematic cross-sectional view of a tube formed from the sheet shown in FIG. 8C.

It will be appreciated that a rectangular shaped sheet of film will form a cylindrical tube whereas a reverse hour glass-shaped sheet (see FIG. 8A) will form a flared tube (see FIG. 8B). Similarly, an arcuate-shaped sheet (see FIG. 8C) will form a trapezoidal-like or curved tube (see FIG. 8D). Virtually any sheet shape can be used provided that when the sheet is formed into a tube, the tube has a first edge 116 defining a first open end 117 and an opposing second edge 118 defining a second open end 119, with the open ends being generally of the same size so the first edge 116 and the second edge 118 can be sealed together. Shaped sheets are useful for forming passages that more closely match the contours of the limb onto which the thermal treatment pack is to be placed.

Figure 7C:
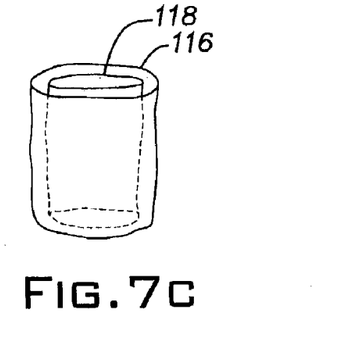
FIG. 7C is a schematic view of the tube in FIG. 7B folded onto itself.

Next, the tube 114 is folded such that the first edge 116 and the second edge 118 are concentric to each other, as shown in FIG. 7C (either the first edge 116 can be outside the second edge 118, or the second edge 118 can be outside the first edge 116). This can be accomplished by turning one of the two open ends of the tube 114 up through the hollow midsection of the tube 114 until the edges are concentric. The two edges are then heat-sealed together using a hot wire or rotary sealing process.

Figure 7D:
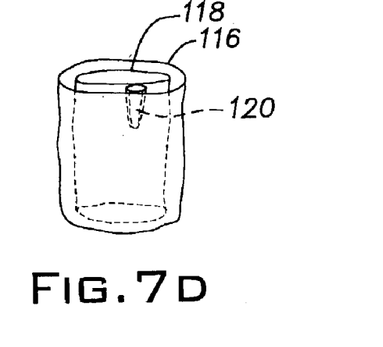
FIG. 7D is a schematic view of the folded tube in FIG. 7C after insertion of a fill valve and sealing.

With reference to FIG. 7D, in the preferred embodiment of the invention, an optional fill valve 120 is installed between the first edge 116 and the second edge 118 before the two edges are sealed together. The fill valve 120 can be a conventional valve, or can simply constitute a small tube of the flexible material through which the temperature-retaining fluid can be inserted. After filling, the pressure exerted by the temperature-retaining fluid against the continuous film is sufficient to collapse the small tube and prevent the temperature-retaining fluid from leaking. A TEFLON insert is preferably inserted through the fill valve 120 to prevent the valve from being sealed closed when the first edge 116 and second edge 118 are sealed together. Next, the first edge 116 and the second edge 118 are sealed together and around the fill valve 120 using a hot wire or rotary sealing process. The TEFLON insert is then removed from the fill valve 120, and a desired amount of a temperature-retaining fluid is pumped through the fill valve 119 into the space between the inner surface 104 and the outer surface 105 of the tubular body 101. The fill valve 120 can be heat-sealed closed after filling, if desired, but this is usually not necessary.

Alternatively, the temperature-retaining fluid can be disposed between the inner surface and the outer surface prior to sealing the first edge to the second edge. This eliminates the need for a fill valve. It is possible to form a thermal treatment pack according to the invention without a fill valve by disposing a temperature-retaining fluid in the space between two concentric tubes of flexible material, which are then radially pinch-sealed together at desired intervals to form a tubular body.

Figure 9A:
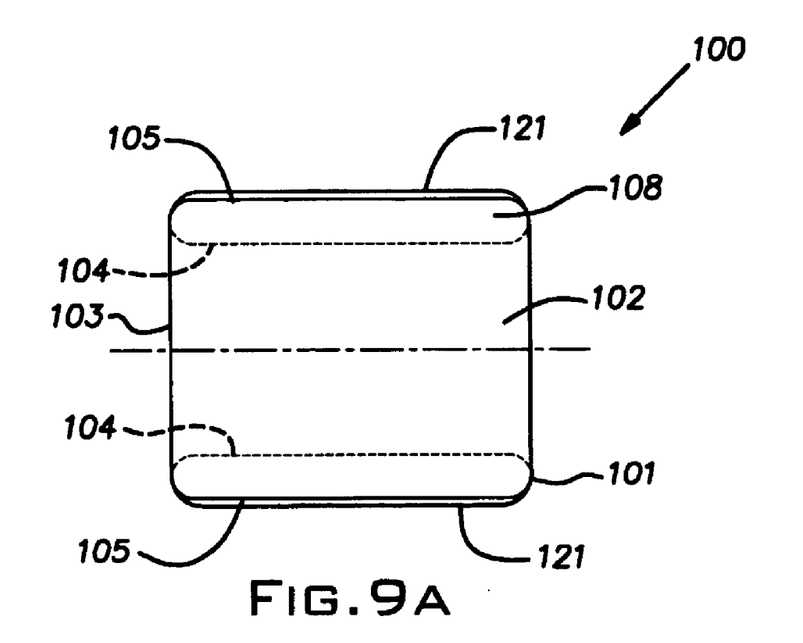
FIG. 9A is a schematic cross-sectional view of an alternative embodiment of a thermal treatment pack according to the invention having an air bladder formed on an outer surface wherein the radial air bladder is in an uninflated state.
Figure 9B:
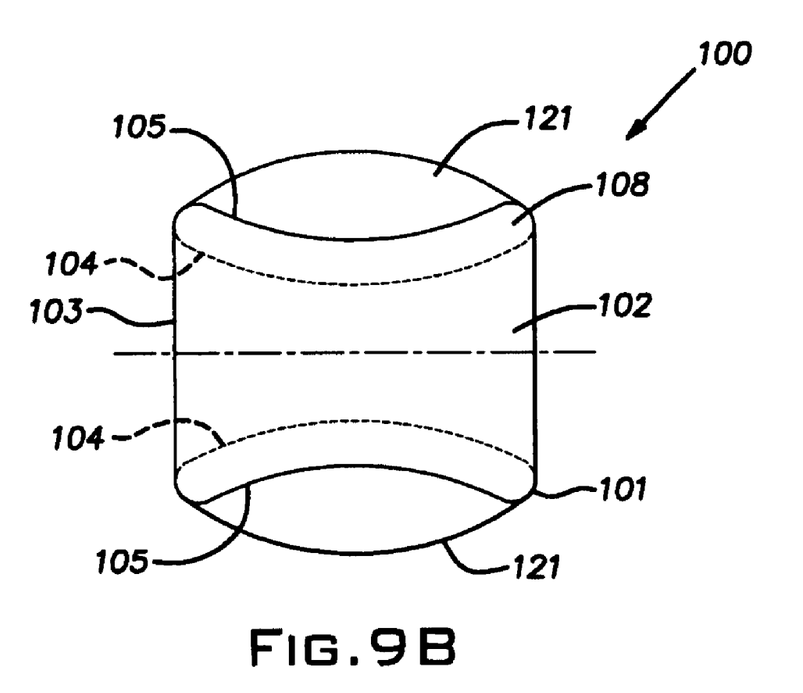
FIG. 9B is a schematic cross-sectional view of an alternative embodiment of a thermal treatment pack according to the invention having an air bladder formed on an outer surface wherein the radial air bladder is in an inflated state.

FIGS. 9A and 9B show cross-sectional views (similar to FIG. 3) of another preferred embodiment of the invention wherein the thermal treatment pack further comprises a selectively pressurizable radial air bladder 121 formed on the outer surface 105 of the tubular body 101. In FIG. 9A, the radial air bladder 121 is in an uninflated state. In FIG. 9B, the radial air bladder 121 is in an inflated state.

The selectively pressurizable radial air bladder 121 is preferably formed by radially heat-sealing a band of flexible film material to the outer surface 105 of the tubular body 101. The band of flexible film material used to form the selectively pressurizable radial air bladder 121 can be heat-sealed to the sheet 113 before it is formed into a tube 114, to the tube 114 before it is formed into the tubular body 101, or to the outer surface 105 of the tubular body 101. A valve 122, which can be of the same configuration as the fill valve 120 for injecting the temperature-retaining fluid into the space between the inner surface and the outer surface or a conventional valve, must be installed to allow for the selective pressurization of the air bladder 121.

Figure 10A:
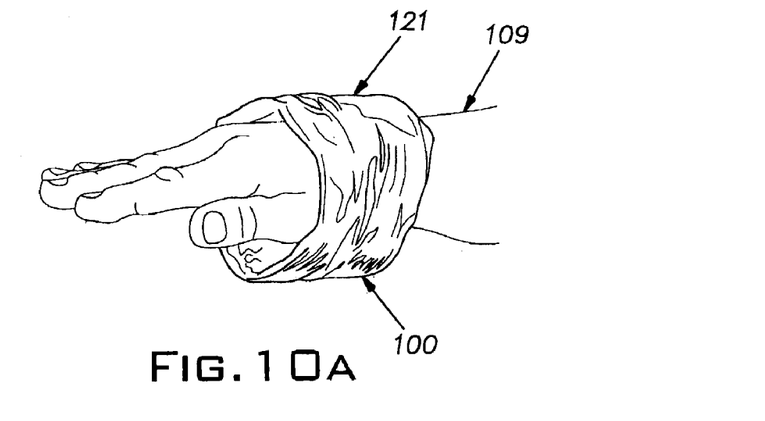
FIG. 10A is a perspective view of an alternative embodiment of a thermal treatment pack according to the invention having an air bladder formed on an outer surface being placed on a user's wrist.

When the thermal treatment pack is provided with a selectively pressurizable radial air bladder, the passage through the tubular body is preferably larger than the user's limb, allowing the thermal treatment pack to be positioned on the user's limb by sliding rather than by rolling. FIG. 10A shows a thermal treatment pack 100 having a radial air bladder 121 as it is being slid onto a user's limb 109, which in FIG. 10A is a wrist. When the thermal treatment pack 100 is properly positioned on the user's limb 109, air is pumped into the radial air bladder 121, which expands the radial air bladder 121 and presses the inner surface 104 of the thermal treatment pack 100 into contact with the user's limb or a fabric layer disposed between the inner surface and the user's limb.

Figure 10B:
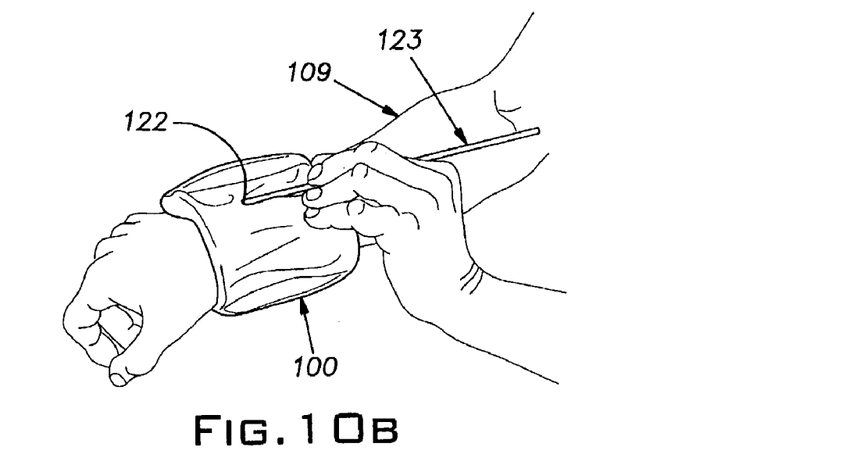
FIG. 10B is a perspective view of the radial air bladder of the thermal treatment pack shown in FIG. 10A being inflated by a user.
Figure 10C:
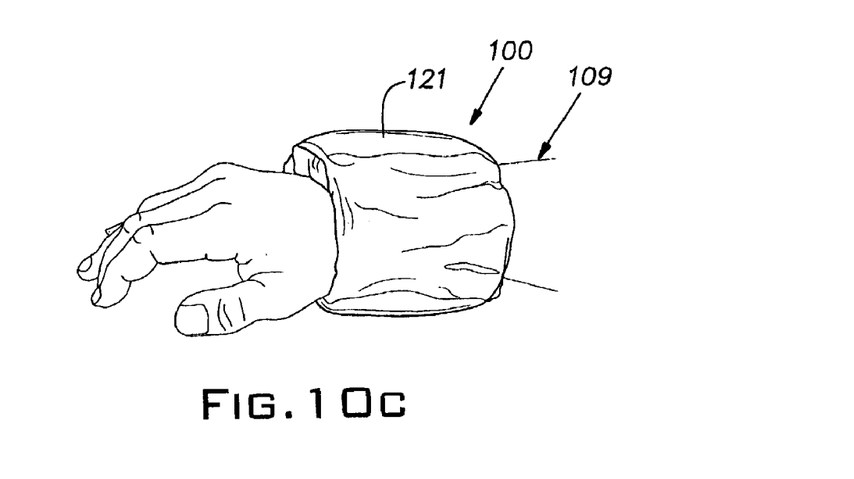
FIG. 10C is a perspective view of the thermal treatment pack shown in FIG. 10A wherein the radial air bladder is in a fully inflated state.

Air can be pumped into the radial air bladder 121 by any means to provide the desired radial compression on the limb. FIG. 10B shows a preferred configuration in which the radial air bladder 121 is selectively pressurized simply by blowing air from one's mouth through a valve 122 into the radial air bladder 121 using flexible tubing 123. The flexible tubing 123 can be reinserted back into the valve 122 to deflate the radial air bladder 121. In FIG. 10C, the radial air bladder 121 of the thermal treatment pack 100 shown in FIG. 10B is shown in a fully inflated state.

A thermal treatment pack according to the invention provides many advantages. The elongated torus-like shaped tubular body allows the thermal treatment pack to be gently rolled onto a user's limb quickly and easily. Alternatively, the diameter of the passage through the thermal treatment pack is greater than the diameter of the user's limb and the thermal treatment pack is provided with a selectively pressurizable radial air bladder that allows the thermal treatment pack to be slid onto the user's limb quickly and easily. The thermal treatment pack can be placed on an injured limb using one hand, and does not require the use of auxiliary attachment means such as straps or wraps. The thermal treatment pack provides radial compression to the limb, which reduces swelling and speeds up the recovery time. And, the thermal treatment pack provides circumferential thermal treatment to an injured limb.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A method of providing thermal treatment to an injured limb comprising:

providing a thermal treatment pack comprising a tubular body having a first opening, a second opening, an inner surface and an outer surface, wherein the first opening, the inner surface and the second opening cooperate to define a passage through the tubular body for receiving the limb, wherein the inner surface and the outer surface of the tubular body are defined by a continuous eversion-limitless film of flexible material, and wherein a non-gaseous temperature-retaining fluid that does not become a hard solid at 32° F. is received between the inner surface and the outer surface of the tubular body;

pre-chilling or pre-heating the thermal treatment pack; inserting the injured limb into the passage through the tubular body of the pre-chilled or pre-heated thermal treatment pack; and positioning the pre-chilled or pre-heated thermal treatment pack at a desired location on the injured limb where thermal treatment is desired.

2. The method according to claim 1 wherein during the positioning step, the film of flexible material everts and the tubular body to rolls onto the injured limb.

3. The method according to claim 1 wherein the thermal treatment pack is pre-chilled to a temperature of about 32° F. or lower before being positioned on the injured limb.

4. The method according to claim 1 wherein the injured limb is wrapped with an insulating fabric before the thermal treatment pack is positioned on the injured limb.

5. The method according to claim 1 wherein the diameter of the passage formed through the tubular body is smaller than the diameter of the injured limb such that the thermal treatment pack provides circumferential thermal treatment and compression when positioned on the injured limb.

6. The method according to claim 1 wherein the temperature-retaining fluid is a gel.

7. The method according to claim 6 wherein the gel is water-based.

8. The method according to claim 7 further comprising a plurality of free-flowing solid structures dispersed in the gel.

9. The method according to claim 8 wherein the free-flowing solid structures comprise water-filled capsules.

10. The method according to claim 1 wherein the continuous film of flexible material comprises a copolymer of polyester and polyurethane.

11. The method according to claim 1 wherein the continuous film of flexible material exhibits a Shore A durometer hardness of greater than or equal to 85 as measured in accordance with the ASTM 2240.00 standard.

12. The method according to claim 1 wherein the continuous film of flexible material has a thickness of from about 3 to about 15 mils.

13. The method according to claim 1 further comprising a fill valve for injecting the temperature-retaining fluid between the inner surface and the outer surface.

14. The method according to claim 1 wherein the temperature-retaining fluid is a water-based gel and the continuous film of flexible material comprises a copolymer of polyester and polyurethane.

15. The method according to claim 14 wherein the continuous film of flexible material exhibits a Shore A durometer hardness of 93±5 as measured in accordance with the ASTM 2240.00 standard.

16. The method according to claim 15 wherein the continuous film of flexible material has a thickness of 5±2 mils.

17. The method according to claim 16 further comprising water-filled capsules dispersed in the temperature-retaining fluid.

18. The method according to claim 17 further comprising a fill valve for injecting the temperature-retaining fluid between the inner surface and the outer surface.

19. The method according to claim 1 wherein the passage through the tubular body is cylindrical, tapered or flared at the first opening and/or second opening.

20. The method according to claim 1 wherein the temperature-retaining fluid is more viscous than water.

21. The method according to claim 1 wherein an insulation layer is disposed on the inner surface and the outer surface of the tubular body.

22. The method according to claim 21 wherein the insulation layer comprises fabric.

23. The method according to claim 1 wherein the passage through the tubular body for the limb has a diameter of 2.5 inches or greater.

24. A method of providing thermal treatment to an injured limb comprising:

providing a thermal treatment pack comprising a tubular body having a first opening, a second opening, an inner surface and an outer surface, wherein the first opening, the inner surface and the second opening cooperate to define a passage through the tubular body for receiving the limb, wherein the inner surface and the outer surface of the tubular body are defined by a continuous eversion-limitless film of flexible material, and wherein a temperature-retaining water-based gel that does not become a hard solid at 32° F. is received between the inner surface and the outer surface of the tubular body;

pre-chilling the thermal treatment pack;

inserting the injured limb into the passage through the tubular body of the pre-chilled thermal treatment pack thereby everting the film of flexible material and allowing the tubular body to roll onto the injured limb; and positioning the pre-chilled thermal treatment pack at a desired location on the injured limb where cold thermal treatment is desired.

25. The method according to claim 24 wherein the injured limb is wrapped with an insulating fabric before the thermal treatment pack is positioned on the injured limb.

26. The method according to claim 24 wherein the diameter of the passage formed through the tubular body is smaller than the diameter of the injured limb such that the thermal treatment pack provides circumferential thermal treatment and compression when positioned on the injured limb.

27. The method according to claim 24 further comprising a plurality of free-flowing solid structures dispersed in the gel.

28. The method according to claim 27 wherein the free-flowing solid structures comprise water-filled capsules.

29. The method according to claim 24 wherein the passage through the tubular body is cylindrical, tapered or flared at the first opening and/or second opening.

30. The method according to claim 24 wherein an insulation layer is disposed on the inner surface and the outer surface of the tubular body.

31. The method according to claim 30 wherein the insulation layer comprises fabric.

* * * * *